United States Patent [19]
Fujino et al.

[11] Patent Number: 5,907,398
[45] Date of Patent: May 25, 1999

[54] PARTICLE DETECTING METHOD AND SYSTEM FOR DETECTING MINUTE PARTICLES ON A WORKPIECE

[75] Inventors: Naohiko Fujino; Junji Kobayashi, both of Tokyo, Japan

[73] Assignee: Mitsubishi Denki Kabushiki Kaisha, Tokyo, Japan

[21] Appl. No.: 08/905,049

[22] Filed: Aug. 1, 1997

[30] Foreign Application Priority Data

Aug. 8, 1996 [JP] Japan ................................ 8-210023

[51] Int. Cl.$^6$ ................................................ G01N 21/00
[52] U.S. Cl. ................................ 356/237.3; 356/237.4
[58] Field of Search ................................ 356/237, 239, 356/237.3–237.5, 237.1, 237.2, 238.1–238.3, 239.1–239.8

[56] References Cited

U.S. PATENT DOCUMENTS

| | | |
|---|---|---|
| 4,772,126 | 9/1988 | Allemand et al. . |
| 5,023,714 | 6/1991 | Lemelson .............................. 356/237.3 |
| 5,157,463 | 10/1992 | Brown et al. ........................... 356/237 |
| 5,517,027 | 5/1996 | Nakagawa et al. . |
| 5,694,214 | 12/1997 | Watanabe et al. ...................... 356/237 |
| 5,715,052 | 2/1998 | Fujino et al. . |

FOREIGN PATENT DOCUMENTS

| | | |
|---|---|---|
| 63-204140 | 8/1988 | Japan . |
| 7-325041 | 12/1995 | Japan . |
| 8-29354 | 2/1996 | Japan . |

OTHER PUBLICATIONS

"Analysis and Evaluation Technology for High Performance Semiconductor Process" (Ultra Clean Technology Series No. 13) Published May 29, 1992—Partial English Translation pp. 111–120.

"Semiconductor Measurement and Evaluation Dictionary" Published Feb. 10, 1994—partial English Translation pp. 474–475.

*Primary Examiner*—Robert H. Kim
*Assistant Examiner*—Amanda Merlino
*Attorney, Agent, or Firm*—Oblon, Spivak, McClelland, Maier & Neustadt, P.C.

[57] ABSTRACT

In a particle detecting method, a light beam is projected on a surface of a workpiece. By a microscope focused on a spot of the light beam, formed is an image of irregularly reflected light irregularly reflected by a minute dust particle lying on the surface of the workpiece. The image of the irregularly reflected light is taken by an image pickup tube disposed at a position corresponding to the eyepiece unit of the microscope. The image of the irregularly reflected light is displayed on a screen of a display tube. The image is analyzed by a computer to determine the position of the minute dust particle on the workpiece in an X-Y plane. Further, the workpiece or the microscope is moved in an X-Y plane to inspect the entire surface of the workpiece.

20 Claims, 6 Drawing Sheets

Time T after

FIG. 3(b)

Time T/2 after

FIG. 3(c)

Time T/2 after

PARTICLE DETECTING METHOD AND SYSTEM FOR DETECTING MINUTE PARTICLES ON A WORKPIECE

BACKGROUND OF THE INVENTION

1. Field Of The Invention

The present invention relates to a particle detecting method which projects a light beam on the surface of a workpiece and determines the position of a minute dust particle on the surface of the workpiece through the observation of changes in the light beam caused by the minute dust particle. The present invention also relates to a particle detecting system which carries out the above particle detecting method.

2. Discussion Of The Background

Defects attributable to dust particles adhering to semiconductor wafers are principal factors which reduce Integrated Circuit (IC) yield in the manufacture of Very Large Scale Integrated (VLSI) circuits, such as 16-Mb DRAMs. Although some minute dust particles may have not been causes of problems in the past, those minute dust particles introduced in the manufacturing process adhere to wafers and have become sources of contamination with the progressive reduction of the width of lines forming patterns. Generally, the size of minute dust particles which will cause problems is a fraction of the minimum width of lines of a VLSI circuit to be fabricated. It is a generally accepted idea that minute dust particles of diameters on the order of 0.1 $\mu$m can not be ignored when fabricating 16-Mb DRAMs, in which the width of the narrowest lines is 0.5 $\mu$m. Such minute dust particles contaminate VLSI circuits, causing the disconnection of circuit patterns and short-circuiting, make VLSI circuits defective and reduce the quality and the reliability of VLSI circuits. Accordingly, it is a key to the improvement of IC yield to detect minute dust particles, to measure and grip accurately and quantitatively the actual state of existence of dust particles on workpieces, and to control dust particles.

A dust particle inspection system capable of detecting dust particles on the surface of a flat workpiece, such as a silicon wafer, and determining the positions of the dust particles has been used for inspecting workpieces. A dust particle detecting method by which a conventional dust particle inspection system detects dust particles will be described hereinafter.

A light-scattering dust particle detecting method is employed by a dust particle inspection system for detecting dust particles. The light-scattering dust particle detecting method scans the surface of a wafer with a light beam, measures the variation of intensity of scattered light with time linearly by a photo-multiplier tube, and detects a dust particle and determines the position of the dust particle from the relation between a moment when a scatter signal is generated upon the reception of scattered light scattered by a fine particle and the position of the scanning light beam on the surface of the wafer at the same moment. Dust particle inspection systems IS-200 and LS-6000 available from Hitachi Electronics Engineering Ltd., Surfscan 6200 available from TENCOR, and dust particle inspection system WIS-9000 available from ESTEK are known as dust particle inspection systems. Measuring principles on which those known dust particle inspection systems operates and the configuration of those dust particle inspection systems are explained in, for example, "ANALYSIS AND EVALUATION TECHNIQUE FOR HIGH PERFORMANCE SEMICONDUCTOR PROCESS", by Semiconductor Basic Technology Research, REALIZE INC., pp. 111–129.

The accuracy of measurement of fine particles of the conventional measuring method using scattered light is limited by noise generated in a measuring system and included in a scatter signal representing light scattered by fine particles. Noise attributable to the surface roughness of a silicon wafer, which is called haze, makes the detection of fine dust particles of 0.10 $\mu$m or below in particle size on the surface of the silicon wafer very difficult. This problem is explained in detail in, "SEMICONDUCTOR MEASUREMENT AND EVALUATION HANDBOOK", by SCIENCE FORUM, pp. 474–479. However, there has not been established any method of detecting minute dust particles of 0.07 $\mu$m, 0.04 $\mu$m and 0.03 $\mu$m in particle size which must be controlled in the manufacture of VLSI circuits, such as 64-Mb, 256-Mb and 1-Gb DRAMs, although those VLSI circuits are expected to be developed and mass-produced in the future, in which the width of the narrowest lines is 0.35 $\mu$m, 0.20 $\mu$m and 0.15 $\mu$m, respectively.

A fine particle measuring method using the scattering of light, which is carried out by the conventional dust particle inspection system, scans the surface of a workpiece, such as a silicon wafer, with a light beam, and detects the variation of the quantity of scattered light linearly by a photodetector, such as a photo-multiplier tube. Therefore, the measured position of a minute dust particle includes an error corresponding to the area of a pixel dependent on the area of a spot formed by the light beam on the surface of the workpiece, and hence a precise determination of the position of the dust particle is impossible. The light beam must be focused on the surface of the workpiece in the smallest possible spot to achieve the highly accurate determination of the position of a dust particle on the surface of the workpiece. However, there is a limit to the reduction of the spot of the light beam. If the light beam is focused in a very small spot, the total length of scanning lines for scanning the entire surface of the workpiece increases, and an increased measuring time is necessary. Usually, the pixel of the current system is 20×200 $\mu$m$^2$. The area of a focused laser beam used by the conventional dust particle inspection system is explained in detail in "ANALYSIS AND EVALUATION TECHNIQUE FOR HIGH PERFORMANCE SEMICONDUCTOR PROCESS", by Semiconductor Basic Technology Research, pp. 111–129.

Figure 5:
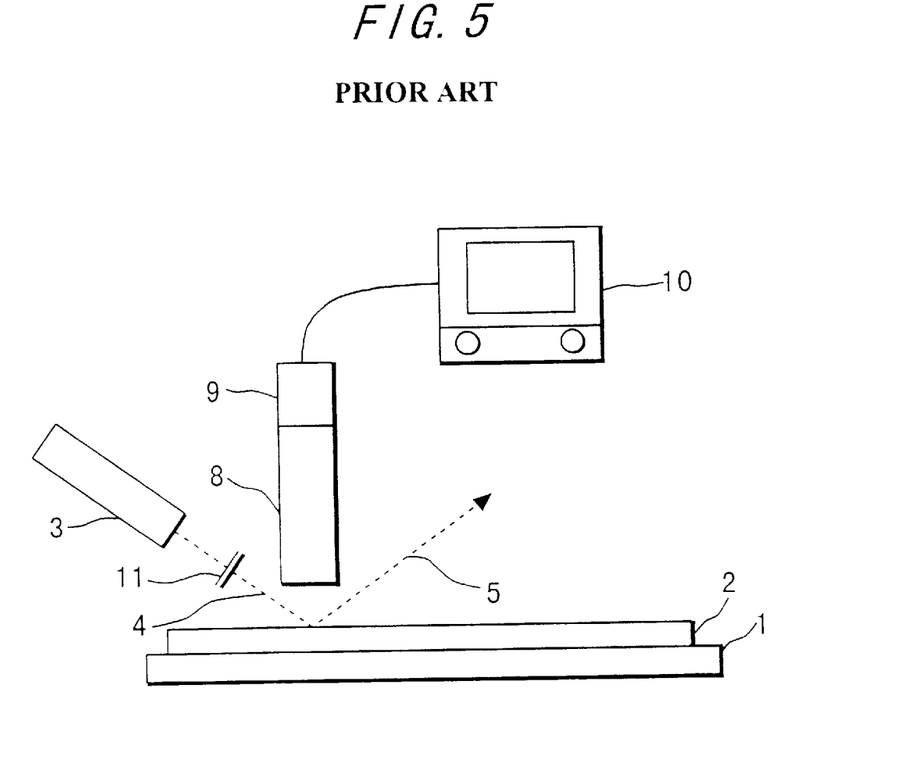
FIG. 5 shows a related particle detecting system.
Figure 6:
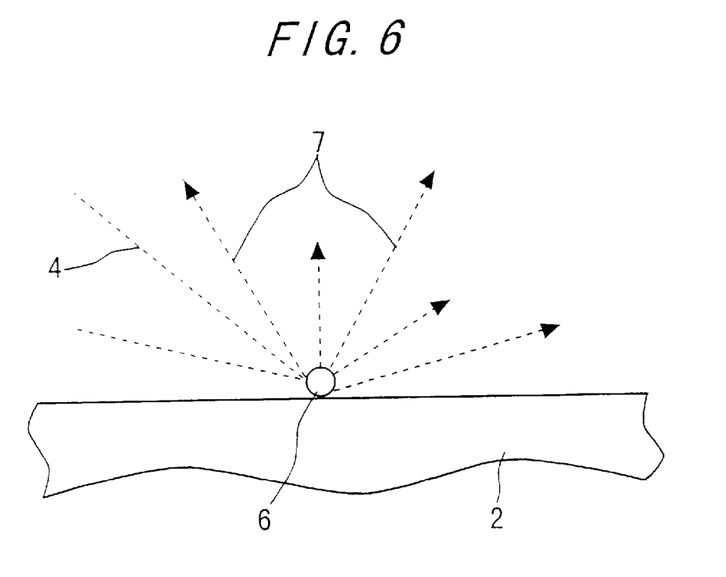
FIG. 6 and FIG. 7 illustrate a mode of projecting the detecting light beam on a workpiece.
Figure 7:
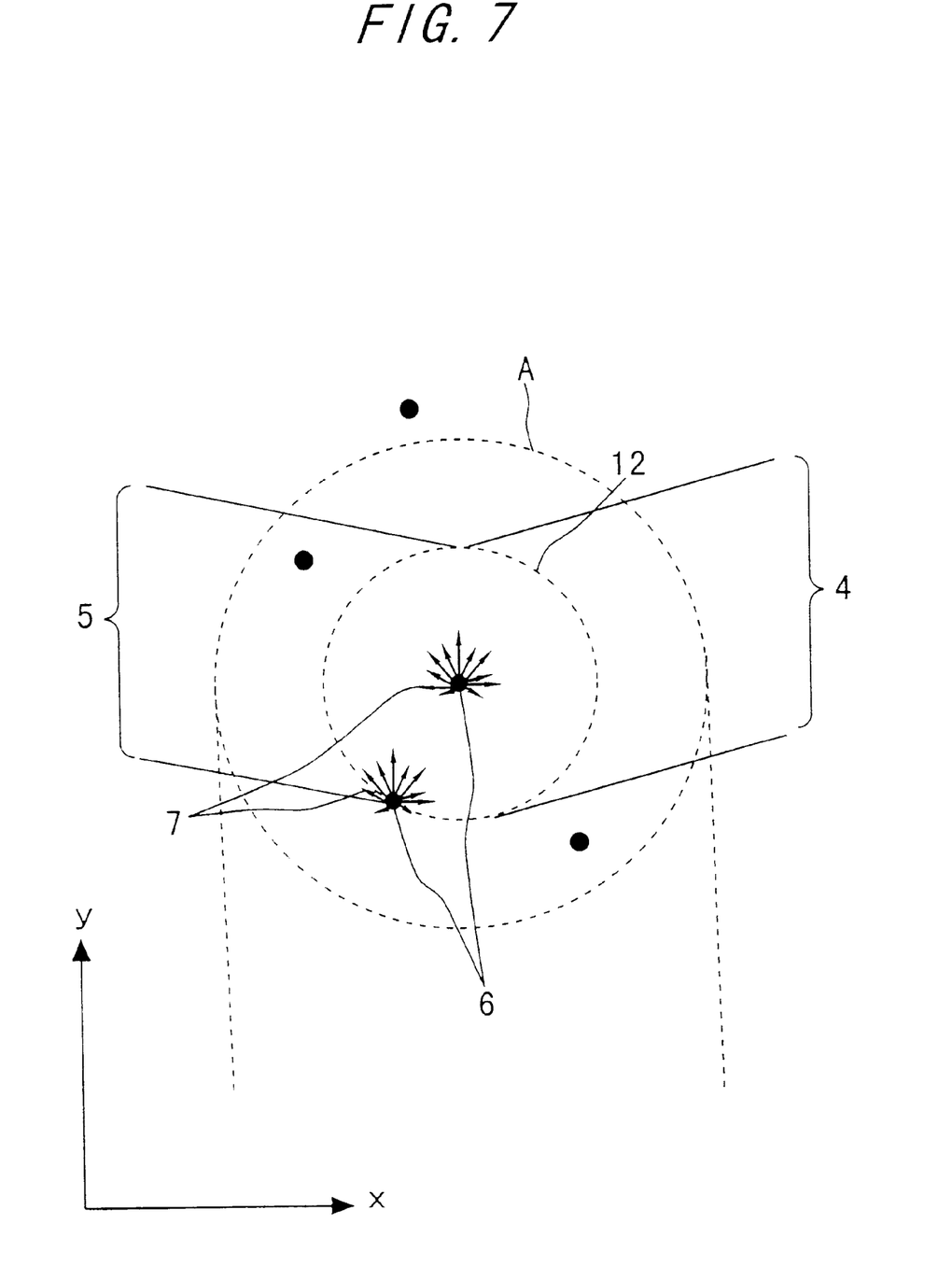

When detecting a minute dust particle of 0.10 $\mu$m or below in particle size, the minute dust particle must be detected at a high sensitivity and at a high S/N ratio, and the position of the dust particle must be determined in a high accuracy. Dust particle detecting methods disclosed in Japan Laid Open Patent Publications (JP-A) Nos. 8-29354 and 7-325041 may be effective in achieving such dust particle detection. These dust particle detecting methods project a light beam on the surface of a wafer, focuses a microscope on a spot formed on the surface of the wafer by the light beam, enlarge scattered light by the microscope, and observe (detect) two-dimensionally a region of the surface of the wafer in the field of view of the microscope by a highly sensitive CCD camera or the like disposed at a dark field position and provided with an image intensifier. Since these methods detect haze, i.e., noise attributable to light scattered by the surface of the wafer, two-dimensionally, the S/N ratio of a detection signal obtained by these methods is higher than that of a detection signal provided by a conventional dust particle inspection system which measures the haze by a photomultiplier tube by detecting integrated light scattered from minute disorder of the surface of the wafer FIG. 5 shows a particle detecting system disclosed in JP-A Nos. 7-325041 and 8-29354. Shown in FIG. 5 are an X-Y stage 1, a workpiece (silicon wafer) 2, an Ar laser 3 for projecting a laser beam on the workpiece 2, a detecting light beam 4 for detecting minute dust particles, reflected light beam 5 reflected by the workpiece 2, a microscope 8 for observing the workpiece 2, a CCD camera 9 with an image intensifier for taking an image of a portion of the workpiece 2 observed by the microscope 8, and a CRT 10 for displaying an image taken by the CCD camera 9. The detecting light beam 4 can be polarized by a polarizing plate 11. FIGS. 6 and 7 illustrate a mode of projecting the detecting light beam 4 on the workpiece. Shown in FIG. 6 and 7 are a dust particle 6 on the workpiece 2, irregularly reflected light 7, and a spot 12 of the detecting light beam 4.

In operation, the silicon wafer 2, i.e., a workpiece, is mounted on the X-Y stage 1. An imaginary coordinate system is set on the silicon wafer 2 on the X-Y stage 1 with reference to a feature in shape of the silicon wafer 2, such as an orientation flat or a notch formed on the silicon wafer 2. A method of setting a coordinate system is described in detail in JP-A No. 7-25118. The detecting light beam 4 is projected on the silicon wafer 2 to form the spot 12 as shown in FIG. 7 on the surface of the silicon wafer 2. An image of the spot 12 magnified by the microscope 8 disposed in a dark field region is taken by the CCD camera 9, and the image of the spot 12 is displayed on the CRT 10 for observation. The microscope 8 is focused on a surface on which the spot 12 is formed. If there are dust particles 6 in the field of view of the microscope 8, i.e., in the spot 12, irregularly reflected light 7 is observed with the X-Y stage 1 at a position represented by coordinates (x, y) (FIG. 7). If any dust particle is not found in the spot 12, the detecting light beam 4 is reflected regularly and the reflected light beam 5 cannot be observed from the dark field position.

In an observation system shown in FIG. 5 and FIG. 7, the field of view A of the microscope 8 disposed at the dark field position includes the spot 12 formed by the detecting light beam 4 on the silicon wafer 2. Since the dust particles 6 in the spot 12 reflect light irregularly in irregularly reflected light 7, the positions of the dust particles 6 can be determined through the observation of the irregularly reflected light 7 by the microscope 8. Experiments proved that the contrast between a portion from which the irregularly reflected light 7 is reflected and a portion from which no irregularly reflected light is reflected is very high, so dust particles of particle sizes of 0.03 $\mu$m or below can clearly be identified, and a detection signal of a satisfactorily high S/N ratio can be obtained. If there is no dust particle 6 in the spot 12, the detecting light beam 4 is substantially perfectly regularly, and hence practically nothing can be observed by the microscope 8 disposed at the dark field position. Therefore, the irregularly reflected light 7 reflected by the dust particles 6 can be observed by the microscope disposed at the dark field position even if the detecting light beam 4 forms the spot 12 in a size far greater than that of the dust particles 6 and, consequently, the positions of the dust particles 6 in the spot 12 can easily be determined in a high accuracy.

As described above, the dust particle detecting system is constructed to observe a portion of a workpiece. Therefore, the method employing the CCD camera needs an additional system which enables the observation of the entire surface of the workpiece if the detection of dust particles on the entire surface of the workpiece is desired.

SUMMARY OF THE INVENTION

The present invention has been made to solve the foregoing problems and it is therefore an object of the present invention to provide a particle detecting method and a particle detecting system capable of detecting minute dust particles of 0.1 $\mu$m or below in size on the entire surface of a workpiece easily and quickly. The term "minute dust particles" as used herein signifies not only dust particles of particle sizes in the range of 0.1 to 0.005 $\mu$m, but also crystalline defects and scratches.

According to one aspect of the present invention, in a particle detecting method, a light beam is projected on a surface of a workpiece. By a microscope focused on a spot of the light beam, formed is an image of irregularly reflected light irregularly reflected by a minute dust particle lying on the surface of the workpiece. The image of the irregularly reflected light is taken by an image pickup tube disposed at a position corresponding to the eyepiece unit of the microscope. The image of the irregularly reflected light is displayed on a screen of a display tube. The image is analyzed by a computer to determine the position of the minute dust particle on the workpiece in an X-Y plane having an x-axis and a y-axis. Further, the workpiece or the microscope is moved in an X-Y plane to inspect the entire surface of the workpiece.

In another aspect of the present invention, in the particle detecting method, the workpiece is mounted on an X-Y stage, and the X-Y stage is moved along the x-axis or the y-axis to enable the observation of the entire surface of the workpiece.

In another aspect of the present invention, in the particle detecting method, the workpiece is mounted on a rotary stage, and the rotary stage is moved linearly by an uni-axial slider to enable the observation of the entire surface of the workpiece.

In another aspect of the present invention, in the particle detecting method, the workpiece or the microscope is moved intermittently in an X-Y plane to inspect the entire surface of the workpiece.

In another aspect of the present invention, in the particle detecting method, the workpiece or the microscope is moved continuously in an X-Y plane to inspect the entire surface of the workpiece.

In another aspect of the present invention, in the particle detecting method, the image pickup tube is a CCD camera.

In another aspect of the present invention, in the particle detecting method, the CCD camera is provided with an image intensifier.

In another aspect of the present invention, in the particle detecting method, the scanning direction of the image pickup tube is substantially perpendicular to the moving direction of the workpiece, and the feed direction of the image pickup tube is reverse to the moving direction of the workpiece.

In another aspect of the present invention, in the particle detecting method, the moving speed of the workpiece is not greater than a divided value obtained by dividing the vertical size or the horizontal size of the displayed field of the display tube by a time required by the image pickup tube for the observation of one frame.

In another aspect of the present invention, in the particle detecting method, the computer decides that the irregularly reflected light is reflected by a dust particle when the interval of the signals representing the irregularly reflected light by the image pickup tube is equal to half a time required for the image pickup tube to complete the observation of one frame.

According to another aspect of the present invention, a particle detecting system comprises means for projecting a light beam on a surface of a workpiece. A microscope is provided which is focused on a spot formed by the light beam on a surface of a workpiece. Also provided is means for moving the workpiece or the microscope to inspect the entire surface of the workpiece.

In another aspect of the present invention, the particle detecting system further comprises an X-Y stage for mounting the workpiece, and the X-Y stage is moved along the x-axis or the y-axis to enable the observation of the entire surface of the workpiece.

In another aspect of the present invention, the particle detecting method further comprises a rotary stage for mounting the workpiece, and a uni-axial slider for sliding the rotary stage. Thereby, the workpiece is moved by the combination of the linear motion of the uni-axial slider and the rotating motion of the rotary stage to enable the observation of the entire surface of the workpiece.

In another aspect of the present invention, in the particle detecting system, the workpiece or the microscope is moved intermittently in an X-Y plane at a pitch not greater than a displayed field of the display tube.

In another aspect of the present invention, in the particle detecting system, the workpiece or the microscope is moved continuously in an X-Y plane in a pitch not greater than a displayed field of the display tube.

In another aspect of the present invention, in the particle detecting system, the scanning direction of the image pickup tube is substantially perpendicular to the moving direction of the workpiece, and the feed direction of the image pickup tube is reverse to the moving direction of the workpiece.

In another aspect of the present invention, the particle detecting system further comprises an image pickup tube disposed at a position corresponding to the eyepiece unit of the microscope, and a display tube for displaying a picture of the irregularly reflected light taken by the image pickup tube.

In another aspect of the present invention, the particle detecting system further comprises a computer for analyzing the picture of the irregularly reflected light taken by the image pickup tube to determine the position of the minute dust particle on the surface of the workpiece.

In another aspect of the present invention, in the particle detecting system, the moving speed of the workpiece is not greater than a divided value obtained by dividing the vertical size or the horizontal size of the displayed field of the display tube by a time required by the image pickup tube for the observation of one frame.

In another aspect of the present invention, in the particle detecting system, the computer decides that the irregularly reflected light is reflected by a dust particle when the interval of the signals representing the irregularly reflected light by the image pickup tube is equal to half a time required for the image pickup tube to complete the observation of one frame.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE PREFERRED EMBODIMENTS

Preferred embodiments of the present invention will be described hereinafter with reference to the accompanying drawings, in which same reference numerals refer to the same or corresponding parts.

FIRST EMBODIMENT

Figure 1:
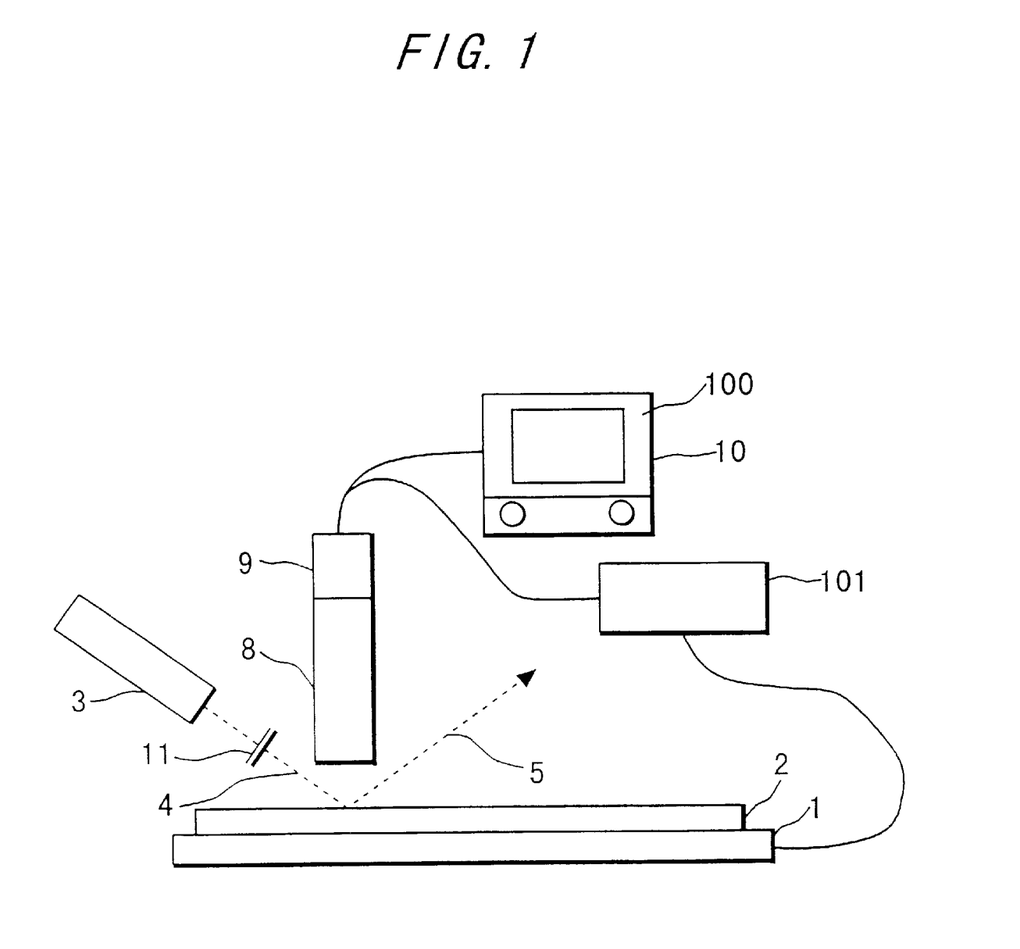
FIG. 1 shows a particle detecting system in a first embodiment according to the present invention.

FIG. 1 shows a particle detecting system in a first embodiment according to the present invention. In FIG. 1, indicated at 101 is a computer for calculating the positional relation between the position at which light is irregularly reflected on a workpiece on a X-Y stage 1, and the position on CRT screen 100 of the CRT display 10. The particle detecting system is similar in construction as the particle detecting system shown in FIG. 5 in other respects. Although an observation region to be evaluated is expressed by the CRT screen 100 herein, practically, a region to be observed is not limited to the CRT screen 100, but signifies all image signals of a region to be evaluated provided by a CCD camera 9. The computer 101 controls a driving mechanism for driving an X-Y stage 1 to move the X-Y stage 1 so that the entire surface of a silicon wafer 2 can fully be observed. A detecting beam 4 forms a spot 12 (shown in FIG. 7) of a size greater than that of the field of view of a microscope 8. A highly accurate imaginary coordinate system is set on the silicon wafer 2 mounted on the X-Y stage 1 with reference to a shape of the silicon wafer 2, such as a flat orientation or to a notch formed in the silicon wafer 2.

The X-Y stage 1 is moved intermittently in an X-direction and a Y-direction at a pitch smaller than the displayed field in the CRT screen 100 corresponding to the field view of the microscope 8 under the control of the computer 101, and irregularly reflected light 7 reflected by dust particles 6 (shown in FIG. 6), if any, and the positions of the dust particles 6 are detected every time the X-Y stage is stopped. Even minute dust particles of 0.03 μm or below in particle size on the entire surface of the silicon wafer can easily and quickly be detected. The positions of the detected dust particles 6 are stored sequentially in a storage means included in the computer 101.

Since the X-Y stage 1 of the first embodiment is moved intermittently in the X-direction and the Y-direction (i.e., the X-Y stage is kept stationary and a driving unit for driving the X-Y stage 1 is actuated intermittently), the particle detecting system takes a long time for measurement. If the X-Y stage 1 is moved continuously, the time necessary for measurement can be saved, and the entire surface of the silicon wafer 2 can be inspected in a time shorter than that necessary when the X-Y stage 1 is moved intermittently.

SECOND EMBODIMENT

If the X-Y stage 1 of the particle detecting system in the first embodiment is moved continuously, some regions of the surface of the silicon wafer 2 cannot be inspected due to the relation between the moving speed of the X-Y stage 1 and the scanning speed of the CCD camera 9. The second embodiment is intended to solve such a problem. In the second embodiment, the moving direction of an X-Y stage 1 and the scanning direction of a CCD camera 9 are substantially perpendicular to each other, and the moving direction of the X-Y stage 1 is reverse to the feed direction of the CCD camera 9 in order that regions which cannot be inspected are reduced to the least possible extent.

Figure 2A:
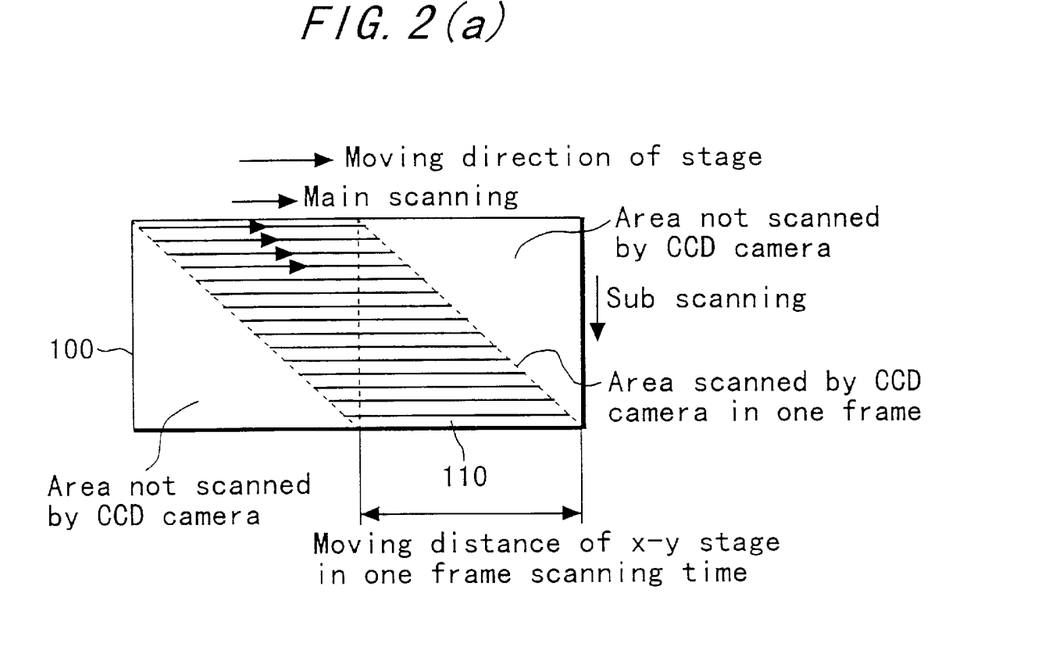
FIGS. 2(a) and 2(b) are diagrammatic views of assistance in explaining a particle detecting method in a second embodiment according to the present invention.
Figure 2B:
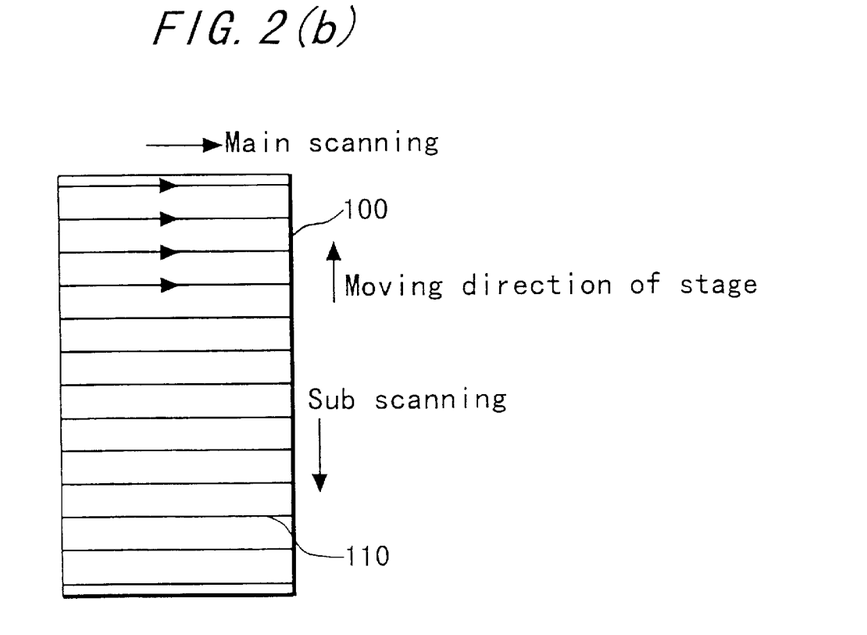

FIGS. 2(a) and 2(b) are diagrammatic views of assistance in explaining a particle detecting method in a second embodiment according to the present invention. In FIGS. 2(a) and 2(b), indicated at 110 are scanning lines along which the CCD camera is moved for scanning. If the X-Y stage 1 is moved continuously, and the CCD camera 9 is controlled so that its scanning direction in which the scanning lines 110 extend is the same as the moving direction of the X-Y stage 1 as shown in FIG. 2(a) for comparison, the CCD camera 9 is reciprocated horizontally for scanning and is fed downward. Therefore, there is a long time difference between a moment when an image of a portion of the silicon wafer 2 corresponding to an upper left-hand corner of the CRT screen 100 is formed and a moment when an image of another portion of the silicon wafer 2 corresponding to a lower left-hand corner of the CRT screen 100 is formed. During this time difference the X-Y stage 1 moves and a portion of the silicon wafer 2 under observation advances. Consequently, the CCD camera 9 scans a rhombic region on the surface of the silicon wafer 2 in an observation time corresponding to one frame, and other regions of the surface of the silicon wafer 2 are not scanned.

In the second embodiment, the scanning direction in which the scanning lines 110 extend and the moving direction of the X-Y stage 1 are substantially perpendicular to each other as shown in FIG. 2(b), and the feed direction of the CCD camera 9 and the moving direction of the X-Y stage 1 are reverse to each other. Therefore, a delay by which the scanning of the CCD camera 9 is delayed behind the movement of the X-Y stage 1 is reduced, and the CCD camera 9 scans a substantially rectangular region on the surface of the silicon wafer 2 in an observation time for one frame. Consequently, only a very small region on the surface of the silicon wafer 2 cannot be scanned. No problem arises if the very small region which was not scanned is added to an inspection region for the next frame. Thus, the entire surface of the silicon wafer 2 can be inspected and the positions of minute dust particles can be determined.

THIRD EMBODIMENT

In the second embodiment, noise generated by the CCD (hereinafter referred to as shot noise) camera may occasionally be mistaken for a dust particle detection signal. The third embodiment is intended to solve such a problem.

FIGS. 3(a), 3(b), 3(c) and 3(d) are diagrammatic views of assistance in explaining a particle detecting method in a third embodiment according to the present invention. In FIGS. 3(a) to 3(d) indicated at 107 is shot noise. A region of the CRT screen 100 corresponds to a region on the X-Y stage which can be displayed on the CRT screen 100 when the X-Y stage 1 is stationary. The moving speeds Vx and Vy at which the X-Y stage 1 is moved continuously at a pitch less than the region of the CRT screen 100 in the X-direction and the Y-direction, respectively, are equal to divided values obtained by dividing the horizontal size Wx and the vertical size Wy of the CRT screen 100 by a time T necessary for the CCD camera 9 to observe one frame; that is, Vx=Wx/T (when the X-Y stage 1 is moved in the X-direction),and Vy=Wy/T (when the X-Y stage 1 is moved in the Y-direction), which are equal to the scanning speed of the CCD camera 9.

Figure 3A:
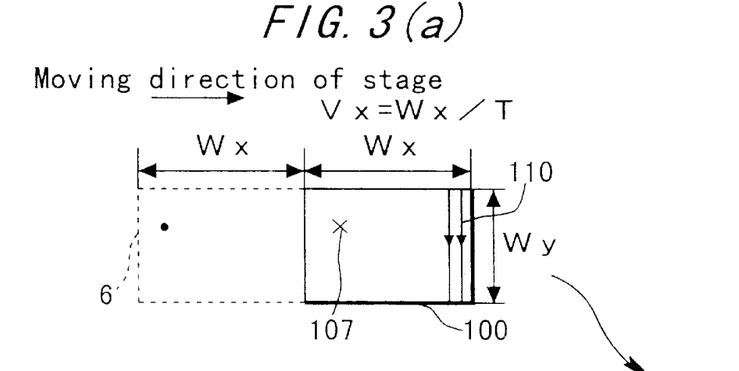
FIGS. 3(a), 3(b), 3(c) and 3(d) are diagrammatic views of assistance in explaining a particle detecting method in a third embodiment according to the present invention.
Figure 3B:
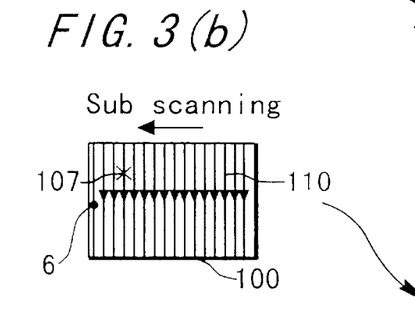
Figure 3C:
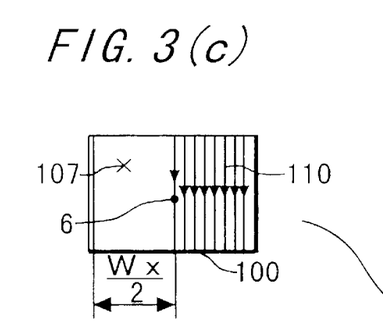
Figure 3D:
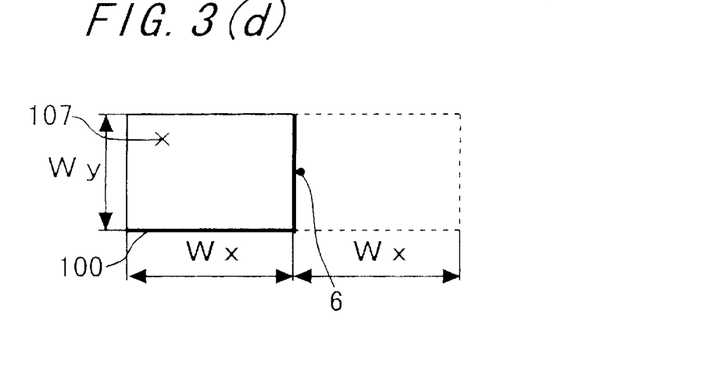

For example, a particle detecting operation is started in a state shown in FIG. 3(a) (frame n). The X-Y stage 1 moves to the right, as viewed in FIG. 3(a), at a speed Vx and therefore a dust particle 6 adhering to the silicon wafer mounted on the X-Y stage 1 moves to the right, as viewed in FIG. 3(a) at the same speed Vx. The CCD camera 9 moves from the right end to the left, as viewed in FIG. 3(a) for scanning along the scanning lines 110 at a speed Vx. FIG. 3(b) shows a state at time T (a time necessary for the CCD camera 9 to complete the observation of one frame) after the state shown in FIG. 3(a). In the state shown in FIG. 3(b), the dust particle 6 has just entered the CRT screen 100 (the frame of the CCD camera 9). The CCD camera 9 moving along the scanning lines 110 detects the shot noise 107, reaches the left end of the CRT screen 100, detects irregularly reflected light 7 reflected by the dust particle 6, and ends the inspection of the frame n. The CCD camera 9 returns to the scanning line 110 at the right end of the CRT screen 100 again and starts scanning a frame n+1. FIG. 3(c) shows a state at time T/2 after the state shown in FIG. 3(b). The dust particle 6 and the CCD camera 9 traveling along the scanning lines 110 approach each other at the speed Vx. Therefore, the CCD camera 9 and the dust particle 6 meet (the CCD camera 9 detects the irregularly reflected light 7 reflected by the dust particle 6) at a position at a distance Wx/2 from one end of the CRT screen 100. The CCD camera 9 reaches the left end of the CRT screen 100 to complete the inspection of the frame n+1 . FIG. 3(d) shows a state at the start of the inspection of a frame n+2. Thus, the irregularly reflected light 7 reflected by the dust particle 6 is detected twice at a time interval of T/2 during the inspection of the frame n and the frame n+1. Therefore, the irregularly reflected light 7 reflected by the dust particle 6 can easily be discriminated from shot noise 107 if the computer 101 is designed so as to recognize detection signals provided at a time interval of T/2 are dust particle detection signals. Since a line connecting the positions of the dust particle 6 in the frames displayed on the CRT screen 100 is parallel to the moving direction of the X-Y stage 1, the detection signal provided upon the detection of the dust particle 6 can also be discriminated from shot noise 107 on the basis of the direction of the line connecting the positions of the dust particle 6 in the frames.

Thus, since the shot noise and the detection signal provided upon the detection of a dust particle can easily be discriminated from each other, a detection signal of a high S/N ratio can be obtained. In the third embodiment, the X-Y stage 1 is moved at the speed Vx or Vy. However, the X-Y stage 1 may be moved at a speed below Vx or Vy to display irregularly reflected light reflected by a single dust particle in a plurality of frames, and the time interval between the detection signals indicating the dust particle in the adjacent frames may be measured to obtain the same effect as the third embodiment.

FOURTH EMBODIMENT

A fourth embodiment employs a rotary stage for supporting a workpiece, while the first to the third embodiments employs the X-Y stage 1.

Figure 4A:
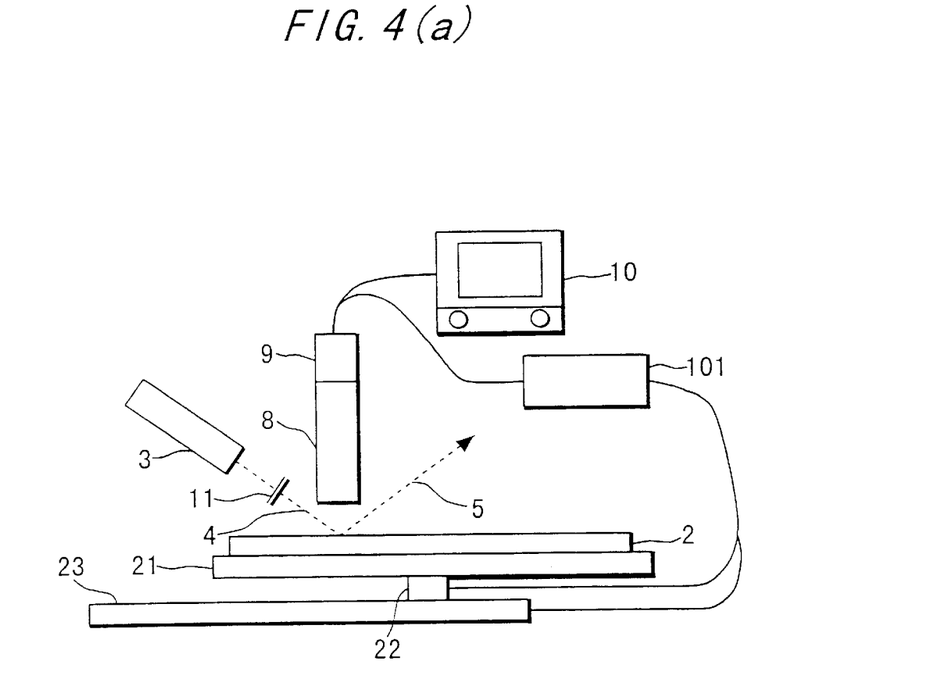
FIGS. 4(a) and 4(b) show a particle detecting system in fourth embodiment according to the present invention.
Figure 4B:
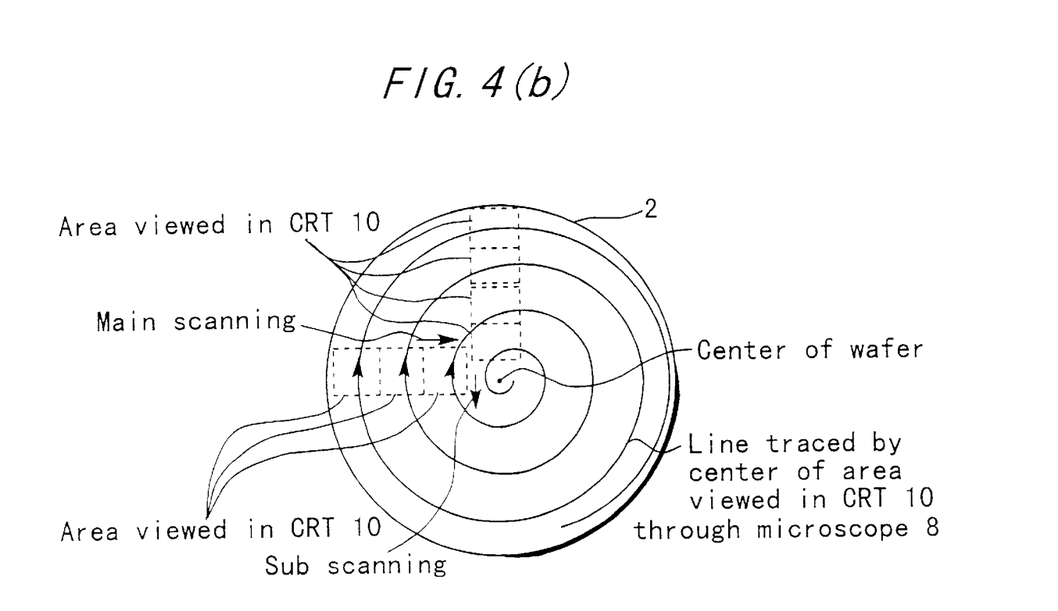

FIGS. 4(a) and 4(b) show a particle detecting system in the fourth embodiment according to the present invention. In FIG. 4(a) indicated at 21 is a rotary stage, at 22 is a spindle and at 23 is a uni-axial slider. A silicon wafer 2 is mounted on the rotary stage 21 with its center coinciding with that of the rotary stage 21. The center of rotation of the rotary stage 21 is on the path of the uni-axial slider 23. The field of view of a microscope 8 is on the path of the uni-axial slider 23.

To start operation, the center of the field of view of the microscope 8 is aligned with the center of the silicone wafer 2. The spindle 22 is driven under the control of a computer 101 for intermittent turning, and the uni-axial slider 23 is driven under the control of the computer 101 for intermittent movement for inspection. If the spindle 22 and the uni-axial slider 23 are moved continuously from a position corresponding to the inner circumference toward the outer circumference of the silicon wafer 2, the entire surface of the silicon wafer 2 can efficiently be inspected along a spiral scanning line as shown in FIG. 4(b), and the positions of minute dust particles can easily and quickly be determined. If a CCD camera 9 is controlled so that the scanning direction of the CCD camera 9 is substantially perpendicular to the rotating direction of the rotary stage 21, and the feed direction of the CCD camera 9 is reverse to the rotating direction of the rotary stage 21, the same effect as that exercised by the second embodiment can be exercised. When the moving speed of the uni-axial slider 23 is reduced gradually as the same moves from a position corresponding to the inner circumference toward the outer circumference of the silicon wafer 2, and the rotating speed of the rotary stage, i.e., and the rotating speed of the spindle 12, is reduced so that the circumferential speed in the field of view of the microscope 8 is equal to the speed Vx or Vy mentioned in connection with the third embodiment, the same effect as that exercised by the third embodiment can be exercised.

Although the X-Y stage 1 is moved to move the silicon wafer 2 in the first to the fourth embodiments, the silicon wafer 2 may be held stationary and the microscope 8 may be mounted on and moved together with the X-Y stage 1.

Although it is described in the description of the first to the fourth embodiments that the irregularly reflected light is detected on the CRT screen 100, actually, the irregularly reflected light is detected by giving image signals provided by the CCD camera 9 (scanning line signals) to the computer 101 and processing the image signals.

As has been described in detail above, according to one aspect of the present invention, since the entire surface of the workpiece can be observed by intermittently moving the workpiece or the microscope in an X-Y plane at a pitch not greater than the range of the CRT screen, the entire surface of the workpiece can easily and quickly be inspected to detect minute dust particles.

According to another aspect of the present invention, the CCD camera employed as the image pickup tube is capable of detecting minute dust particles in a high accuracy.

According to another aspect of the present invention, the CCD camera provided with the image intensifier is capable of detecting minute dust particles at a high sensitivity.

According to another aspect of the present invention, the workpiece is mounted on the X-Y stage, and the X-Y stage is moved along the x-axis or the y-axis so that the entire surface of the workpiece can be observed. Therefore, the entire surface of the workpiece can easily and quickly be inspected to detect minute dust particles.

According to another aspect of the present invention, since the workpiece is moved by the combination of the linear motion of the uni-axial slider and the rotary motion of the rotary stage so that the entire surface of the workpiece can be observed, the entire surface of the workpiece can easily and quickly be inspected to detect minute dust particles.

According to another aspect of to the present invention, since the workpiece or the microscope is moved continuously at a pitch not greater than the range of the CRT screen in an x-y plane so that the entire surface of the workpiece can be observed, the entire surface of the workpiece can easily and quickly be inspected to detect minute dust particles.

According to another aspect of the present invention, since the CCD camera is placed so that the direction of movement of the X-Y stage or the direction of rotation of the rotary stage is substantially perpendicular to the scanning direction of the CCD camera, and the direction of movement of the X-Y stage or the direction of rotation of the rotary stage is reverse to the feed direction of the CCD camera, the entire surface of the workpiece can easily and quickly be inspected to detect minute dust particles.

According to another aspect of the present invention, since the moving speed of the X-Y stage or the circumferential speed of the rotary stage is not greater than a divided value obtained by dividing the vertical size or the horizontal size of the CRT screen by a time required by the CCD camera for the observation of one frame, the entire surface of the workpiece can easily and quickly be inspected to detect minute dust particles.

According to another aspect of the present invention, since the computer decides that the irregularly reflected light is reflected by a dust particle when the duration of a signal representing the detected irregularly reflected light and provided by the CCD camera is equal to half a time necessary for the CCD camera to complete the observation of one frame, the irregularly reflected light can easily be discriminated from shot noise and the entire surface of the workpiece can easily and quickly be inspected to detect minute dust particles.

According to another aspect of the present invention, the particle detecting system, which detects a minute dust particle by either of the particle detecting methods as described above, is capable of easily and quickly inspecting the entire surface of the workpiece to detect minute dust particles.

Obviously, numerous additional modifications and variations of the present invention are possible in light of the above teachings. It is therefore to be understood that within the scope of the appended claims, the invention may be practiced otherwise than as specifically described herein.

What is claimed is:

1. A method of detecting a particle, comprising the steps of:

projecting a light beam on a surface of a workpiece;

forming an image of irregularly reflected light irregularly reflected by a minute dust particle lying on said surface of said workpiece from a dark field by a microscope focused on a spot of said light beam;

taking an image of said irregularly reflected light by an image pickup means disposed at a position corresponding to an eyepiece unit of said microscope;

displaying said image of said irregularly reflected light on a screen of a display means; and analyzing said image by a computer to determine a position of said minute dust particle on said workpiece in an X-Y plane having an x-axis and y-axis, wherein at least one of said workpiece and said microscope is continuously moved in said X-Y plane to inspect an entire surface of said workpiece, and wherein said image pickup means scans a substantially rectangular region on said surface of said workpiece in a time required for said image pickup means for observation of one frame.

2. The method as set forth in claim 1, wherein said workpiece is mounted on said X-Y plane, and said X-Y plane is moved along at least one of said x-axis and said y-axis to enable observation of said entire surface of said workpiece.

3. The method as set forth in claim 1, wherein said image pickup means comprises a CCD camera.

4. The method as set forth in claim 3, wherein said CCD camera includes an image intensifier.

5. The method as set forth in claim 1, wherein a scanning direction of said image pickup means is substantially perpendicular to a moving direction of said workpiece, and a feed direction of said image pickup means is reverse to said moving direction of said workpiece.

6. The method as set forth in claim 1, wherein a moving speed of said workpiece is not greater than a divided value obtained by dividing at least one of a vertical size and a horizontal size of a displayed field of said display tube by a time required by said image pickup means for observation of one frame.

7. The method as set forth in claim 1, wherein said computer decides that said irregularly reflected light is reflected by a dust particle when an interval of the signals representing said irregularly reflected light by said image pickup means is equal to half a time required for said image pickup means to complete observation of one frame.

8. The method as set forth in claim 1, wherein said image pickup means scans the entire surface of said workpiece by scanning substantially rectangular regions in succession.

9. A particle detecting system, comprising:
means for projecting a light beam on a surface of a workpiece; and
a microscope focused from a dark field on a spot formed by said light beam on said surface of said workpiece;
means for continuously moving at least one of said workpiece and said microscope to inspect an entire surface of said workpiece; and
an image pickup means disposed at a position corresponding to an eyepiece of said microscope,
wherein said image pickup means scans a substantially rectangular region on said surface of said workpiece in a time required by said image pickup means for observation of one frame.

10. A particle detecting system as set forth in claim 9, further comprising:
an X-Y plane having an x-axis and a y-axis for mounting said workpiece, said X-Y plane being moved along at least one of said x-axis and said y-axis to enable observation of an entire surface of said workpiece.

11. A system as set forth in claim 9,
wherein a scanning direction of image pickup means is substantially perpendicular to a moving direction of said workpiece, and a feed direction of said image pickup means is reverse to said moving direction of said workpiece.

12. A system as set forth in claim 9, further comprising:
a display tube means for displaying a picture of irregularly reflected light taken by said image pickup means.

13. A system as set forth in claim 12, further comprising:
a computer for analyzing said picture of said irregularly reflected light taken by said image pickup means to determine a position of a minute dust particle on said surface of said workpiece.

14. A system as set forth in claim 13, wherein a moving speed of said workpiece is not greater than a divided value obtained by dividing at least one of a vertical size and a horizontal size of a displayed field of said display tube by a time required by said image pickup means for observation of one frame.

15. A system as set forth in claim 13, wherein said computer decides that said irregularly reflected light is reflected by a dust particle when an interval of the signals representing said irregularly reflected light by said image pickup means is equal to half a time required for said image pickup means to complete observation of one frame.

16. A method of detecting a particle, comprising the steps of:
projecting a light beam on a surface of a workpiece;
forming an image of irregularly reflected light irregularly reflected by a minute dust particle lying on said surface of said workpiece from a dark field by a microscope focused on a spot of said light beam;
taking an image of said irregularly reflected light by an image pickup means disposed at a position corresponding to an eyepiece unit of said microscope;
displaying said image of said irregularly reflected light on a screen of a display tube; and
analyzing said image by a computer to determine a position of said minute dust particle on said workpiece in an X-Y plane having an x-axis and y-axis,
wherein at least one of said workpiece and said microscope is moved in said X-Y plane to inspect an entire surface of said workpiece, and
wherein a scanning direction of said image pickup means is substantially perpendicular to a moving direction of said workpiece, and a feed direction of said image pickup means is reverse to said moving direction of said workpiece.

17. A method of detecting a minute particle, comprising the steps of:
projecting a light beam on a surface of a workpiece mounted on a rotary stage, said rotary stage being mounted on an uni-axial slider;
forming an image of irregularly reflected light irregularly reflected by a minute dust particle lying on said surface of said workpiece from a dark field by a microscope focused on a spot of said light beam;
taking an image of said irregularly reflected light by an image pickup means disposed at a position corresponding to an eyepiece unit of said microscope;
displaying said image of said irregularly reflected light on a screen of a display tube; and
analyzing said image by a computer to determine a position of said minute dust particle on said workpiece,
wherein said rotary stage is continuously rotated and moved linearly by said uni-axial slider to inspect an entire surface of said workpiece, and
wherein said image pickup means scans a substantially rectangular region on said surface of said workpiece in a time required by said image pickup means for observation of one frame.

18. The method as set forth in claim 17, wherein a scanning direction of said image pickup means is substantially perpendicular to a rotating direction of said workpiece, and a feed direction of said image pickup means is reverse to said rotating direction of said workpiece.

19. A particle detecting system, comprising:
a rotary stage for mounting a workpiece;
an uni-axial slider for sliding said rotary stage;
means for projecting a light beam on said surface of a workpiece;

a microscope focused from a dark field on a spot formed by said light beam on said surface of said workpiece to form an image of irregularly reflected light irregularly reflected by a minute dust particle lying on said surface of said workpiece;

an image pickup means disposed at a position corresponding to an eyepiece of said microscope; and means for rotating and sliding said rotary stage on said uni-axial slider to inspect an entire surface of said workpiece;

wherein said image pickup means scans a substantially rectangular region on said surface of said workpiece in a time required by said image pickup means for observation of one frame.

20. A system as set forth in claim 19, wherein a scanning direction of said image pickup means is substantially perpendicular to a rotating direction of said workpiece, and a feed direction of said image pickup means is reverse to said rotating direction of said workpiece.

* * * * *